Figure 1:
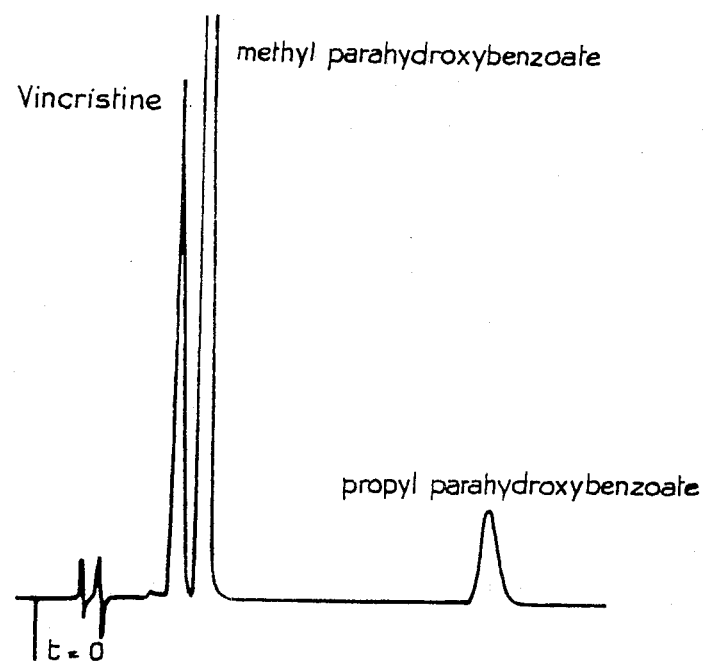

United States Patent [19]

Leverd et al.

[11] Patent Number: 4,966,903
[45] Date of Patent: Oct. 30, 1990

[54] STABLE AQUEOUS SOLUTION OF VINCRISTINE SULFATE

[75] Inventors: Elie Leverd; Michel Bauer; Serge Basquin, all of Castres, France

[73] Assignee: Pierre Fabre Medicament, Paris, France

[21] Appl. No.: 257,148

[22] Filed: Oct. 13, 1988

Related U.S. Application Data

[63] Continuation of Ser. No. 41,407, Apr. 23, 1987, abandoned.

[30] Foreign Application Priority Data

Apr. 25, 1986 [FR] France .............................. 86 06030

[51] Int. Cl.$^5$ .............................................. A61K 31/44
[52] U.S. Cl. ..................................................... 514/283
[58] Field of Search ......................................... 514/283

[56] References Cited

U.S. PATENT DOCUMENTS 3,749,784  7/1973  Johnson ............................... 514/283
4,619,935  10/1986  Robison ............................... 514/283
4,628,047  12/1986  Sakurai et al. ....................... 514/34

FOREIGN PATENT DOCUMENTS 3324964A  1/1984  Fed. Rep. of Germany ...... 514/283
1254057  11/1971  United Kingdom ................ 514/283

*Primary Examiner*—Jerome D. Goldberg
*Attorney, Agent, or Firm*—Fleit, Jacobson, Cohn, Price, Holman & Stern

[57] ABSTRACT

The invention relates to a stable aqueous solution of vincristine sulfate comprising:

(a) a therapeutically effective amount of vincristine sulfate;
(b) 0.1% to 2.2% (w/v) of glycocoll;
(c) a 0.05M to 0.2M phosphate buffer based on monopotassium phosphate, and phosphoric acid, for fixing the pH of the solution at 4.15±0.15;
(d) an effective and pharmacologically compatible amount of an antimicrobial preservative; and
(e) water for injectable preparations.

3 Claims, 4 Drawing Sheets

FIG_1

FIG_2

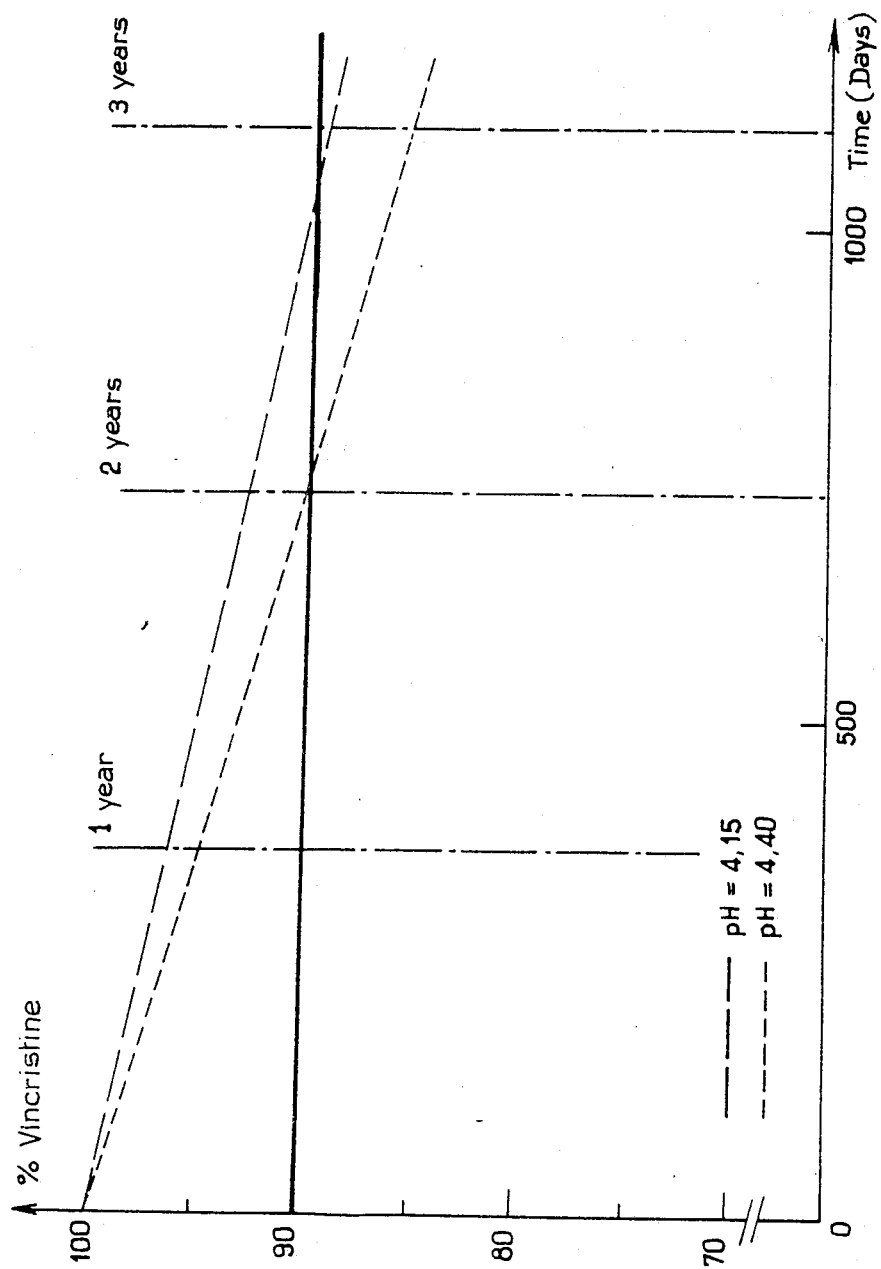
FIG_4

STABLE AQUEOUS SOLUTION OF VINCRISTINE SULFATE

This is a continuation of Ser. No. 041,407, filed 4-23-87, now abandoned.

The present invention relates to a stable aqueous solution of vincristine sulfate.

The Vinca alkaloids are very widely used in medical therapy. Among these, the dimers of indolic structure, in particular vincristine, show valuable properties in the field of cancerology. More particularly, vincristine sulfate, administered intravenously in the form of an injectable preparation, gives excellent results in this field.

Until recent years, this injectable preparation was always presented in the form of a lyophilizate, essentially because of the problems associated with the instability of the molecule in aqueous solution.

More recent studies, illustrated by British Patent Document No. A-2 125 292 for example, have been concerned with stable aqueous compositions of alkaloids, such as vincristine, which contain, as excipients, polyols, an acetate buffer for fixing the pH of the composition within a particular range, and also antimicrobial agents.

The object of the present invention was to develop a novel injectable formulation of vincristine sulfate in aqueous solution with a particularly high stability.

This novel formulation, to which the present invention relates, consists of a stable aqueous solution of vincristine sulfate which comprises:

(a) a therapeutically effective amount of vincristine sulfate;
(b) 0.1% to 2.2% (w/v) of glycocoll;
(c) a 0.05M to 0.2M phosphate buffer based on monopotassium phosphate, and phosphoric acid, for fixing the pH of the solution at 4.15±0.15;
(d) an effective and pharmacologically compatible amount of an antimicrobial preservative; and
(e) water for injectable preparations.

The first essential constituent of the aqueous composition according to the invention is glycocoll (glycine). This is an amino acid—aminoacetic acid—which serves to adjust the isotonicity of the injectable solution. The glycocoll is present in the composition according to the invention in a proportion of 0.1 to 2.2% (w/v), the upper limit of 2.2% by weight/volume corresponding to the preparation of a solution which is isoosmotic with blood.

The second essential constituent of the composition according to the invention is a phosphate buffer based on monopotassium phosphate, in association with phosphoric acid. The phosphate buffer can have a molarity of between 0.05M and 0.2M and preferably a molarity of the order of 0.1M. The purpose of this combination of phosphate buffer and phosphoric acid is to fix the pH of the aqueous solution at a value of 4.15±0.15, which represents the pH for optimum stability of the composition at +4° C. The analytical results indicated below clearly show that deviations from this value cause a very rapid decrease in the stability of the solution.

The composition according to the invention also contains antimicrobial preservatives. They can be used individually or in association with one another, in an effective and pharmacologically compatible amount. By way of example, these antimicrobial preservatives will advantageously be selected from the list given below, which also specifies the maximum use levels:

| | |
|---|---|
| methyl parahydroxybenzoate | 1.5%° (w/v) |
| propyl parahydroxybenzoate | 1.5%° (w/v) |
| phenol | 5%° (w/v) |
| cresols | 3%° (w/v) |
| mercury derivatives | 0.1%° (w/v) |
| benzyl alcohol | 10%° (w/v) |

To illustrate the subject of the present invention, a particular example of a stable aqueous solution of vincristine sulfate is now indicated below; it corresponds to the following formulation:

| | |
|---|---|
| vincristine sulfate | 1 mg |
| methyl parahydroxybenzoate | 1.275 mg |
| propyl parahydroxybenzoate | 0.225 mg |
| glycocoll | 18.900 mg |
| 0.1 M phosphate buffer, pH = 4.5 | 0.200 ml |
| phosphoric acid q.s. | pH = 4.15 |
| water for injectable preparations ad | 1 ml |

In view of the solubility characteristics of each of these constituents in water, the preparation of a solution of this type does not call for any particular comment. Nevertheless, because of the sensitivity of vincristing sulfate to heat, sterilization of the solution is effected by filtration on a membrane of porosity 0.2 μm.

The solution can be packaged in a colorless or brown glass ampoule or in a bottle which is also made of glass and is fitted with a stopper made of a carefully chosen elastomer.

Analytical study as a function of temperature and pH—Optimization within the limits of the Arrhenius model Study of the forced degradation of vincristine sulfate in solution was followed by high performance liquid chromatography.

The conditions were as follows:

| | | |
|---|---|---|
| Column: Microbondapak ® (WATERS), L = 30 cm, | | |
| $d_i$ = 4.2 mm, packed with octadecylsilane (C 18 - 10 μm) | | |
| Eluent: | water | 650 ml |
| | acetonitrile | 350 ml |
| | potassium chloride | 7.45 g |
| | N hydrochloric acid | 15 ml |

FIG. 1 shows the standard chromatogram of the injectable solution prepared according to the above-mentioned formulation.

Figure 2:
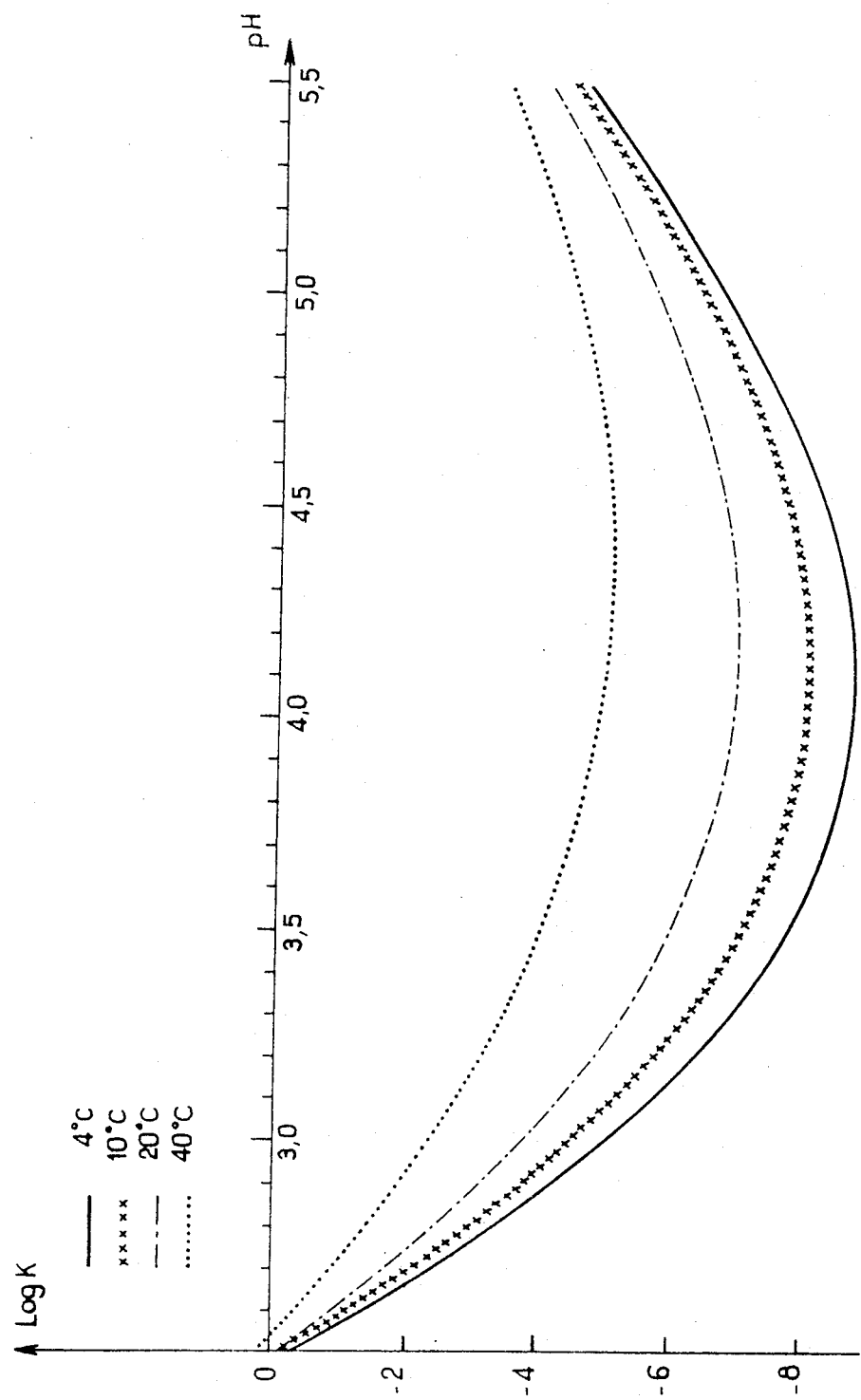

Analysis of the experimental points shows that the degradation of vincristine sulfate in solution follows a first order kinetics law:

$$\text{Log}\frac{C}{C_0} = -kt \quad (1)$$

where
C = concentration of undegraded vincristine sulfate at time (t) in mol/l
$C_0$ = initial concentration of vincristine sulfate in mol/l
t = time in seconds
k = degradation kinetics constant of vincristine sulfate in $s^{-1}$; this constant k is a function of the temperature and pH of the solution in question; it obeys the classical ARRHENIUS law:

$$\text{Log } k(T, \text{pH}) = \text{Log } k_O(T, \text{pH}) - \frac{E_A(\text{pH})}{RT} \quad (2)$$

where:
- $E_A$ is the activation energy of the degradation process in $\text{kcal.mol}^{-1}$, which is a function of the pH of the solution in question
- $k_0$ is the frequency factor, in $s^{-1}$, associated with the activation entropy of the transition state of the degradation process, which is also a function of the pH of the solution in question
- T = absolute temperature in degrees KELVIN (°K)
- R = gas constant, i.e. 0.00198 in $\text{kcal.mol}^{-1}.°K^{-1}$ FIG. 2 shows the variation (*) in k as a function of pH for various temperatures (4° C., 10° C., 20° C., 40° C.).

(*) N.B.: The curves shown are the result of using a polynomial empirical formula of the type:

$y = a_3x^3 + a_2x^2 + a_1x + a_0$, the parameters $a_0$, $a_1$, $a_2$ and $a_3$ being adjusted by the method of least squares on the basis of the experimental values.

Figure 3:
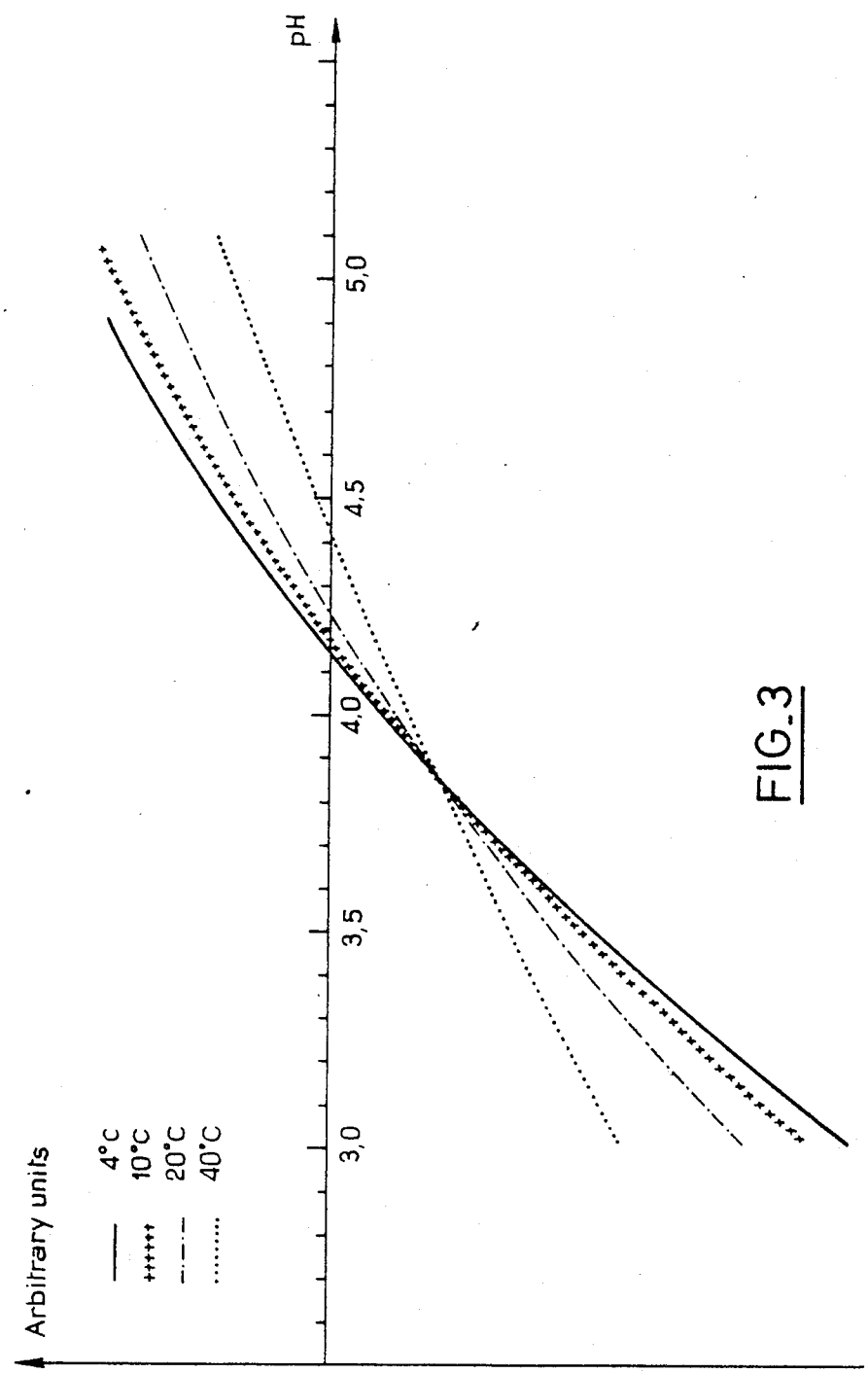

FIG. 3 shows the derivative:

$$\frac{\delta \text{Log } k(T, \text{pH})}{\delta \text{pH}}$$

as a function of pH for the same series of temperatures.

It can be seen that, for storage at 4° C., the optimum $$\left( \frac{\delta \text{Log } k}{\delta \text{pH}} = 0 \right)$$

is reached at a pH of 4.15±0.15.

On the basis of these conditions, it is possible to predict a profile for the decrease in the level of vincristine sulfate in the injectable solution, stored at 4° C., which has the shape shown in FIG. 4 (about 7.5% degradation over 2 years).

For comparison, the change in an injectable solution buffered at pH 4.4 and kept at 4° C. is given on the same graph.

What is claimed is:

1. A stable aqueous solution of vincristine sulfate for parenteral administration, consisting essentially of
   (a) an oncolytically effective amount of vincristine sulfate;
   (b) 0.1% to 2.2% (w/v) of glycocoll;
   (c) a 0.05M to 0.2M phosphate buffer based on monopotassium phosphate, and phosphoric acid, for fixing the pH of the solution at 4.15±0.15;
   (d) an effective and pharmacologically compatible amount of an antimicrobial preservative; and
   (e) water for injectable preparations.

2. A solution as claimed in claim 1, wherein the preservative is selected from the following list of products, which specifies the maximum use levels:

| | |
|---|---|
| methyl parahydroxybenzoate | 1.5%° (w/v) |
| propyl parahydroxybenzoate | 1.5%° (w/v) |
| phenol | 5%° (w/v) |
| cresols | 3%° (w/v) |
| mercury derivatives | 0.1%° (w/v) |
| or benzyl alcohol | 10%° (w/v) |

3. A solution as claimed in claim 1, which corresponds to the following composition:

| | |
|---|---|
| vincristine sulfate | 1 mg |
| methyl parahydroxybenzoate | 1.275 mg |
| propyl parahydroxybenzoate | 0.225 mg |
| glycocoll | 18.900 mg |
| 0.1M phosphate buffer, pH = 4.5 | 0.200 ml |
| phosphoric acid q.s. | pH = 4.15 |
| water for injectable preparations ad | 1 ml. |

* * * * *